United States Patent [19]

Stahly

[11] Patent Number: 5,302,752
[45] Date of Patent: Apr. 12, 1994

[54] ACETIC ACID DERIVATIVES AND THEIR PRODUCTION

[75] Inventor: G. Patrick Stahly, Baton Rouge, La.

[73] Assignee: Ethyl Corporation, Richmond, Va.

[21] Appl. No.: 509,231

[22] Filed: Apr. 16, 1990

Related U.S. Application Data

[63] Continuation-in-part of Ser. No. 428,918, Oct. 30, 1989, abandoned.

[51] Int. Cl.$^5$ .............................................. C07C 53/34
[52] U.S. Cl. ................................... 562/496; 562/493
[58] Field of Search ................................ 562/493, 496

[56] References Cited

U.S. PATENT DOCUMENTS

| | | | |
|---|---|---|---|
| 4,173,706 | 11/1979 | Mathey et al. | 562/493 X |
| 4,238,413 | 12/1980 | Tang et al. | 562/496 X |
| 4,268,687 | 5/1981 | Tang et al. | 562/496 X |
| 4,433,160 | 2/1984 | Amano et al. | 562/493 X |
| 4,469,885 | 9/1984 | Mueller et al. | 562/493 X |
| 4,501,895 | 2/1985 | Mueller et al. | 562/493 X |
| 4,567,053 | 1/1986 | Lindley | 562/496 UX |

OTHER PUBLICATIONS

C.A., 81, 91543r, 1974.
C.A., 100, 203126b, 1984.
C.A., 106, 10853t, 1987.
C.A., 96, 199564x, 1982.

Primary Examiner—Paul F. Shaver
Attorney, Agent, or Firm—Richard J. Hammond

[57] ABSTRACT

Compounds of formula

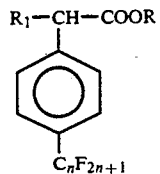

or

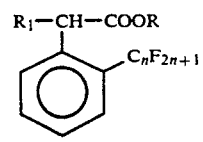

where n is an integer from 1 to 12, R and $R_1$ are the same or different and are hydrogen or $C_1$ to $C_6$ linear or branched alkyl as well as their physiologically active salts and amides thereof and the enantiomers, mixtures and racemates are disclosed. Intermediates useful in preparing the above compounds are also disclosed as are processes for preparing these compounds.

6 Claims, No Drawings

ACETIC ACID DERIVATIVES AND THEIR PRODUCTION

TECHNICAL FIELD

This application is a Continuation-in-Part of copending application Ser. No. 428,918 filed Oct. 30, 1989, now abandoned. This invention relates in general to perfluoroalkyl aromatic compounds. More particularly, this invention relates to a new class of perfluoroalkyl substituted compounds from which perfluoroalkyl aromatic compounds can be readily produced and to novel methods by which such perfluoroalkyl substituted compounds may be prepared.

Perfluoroalkylated aromatic and heterocyclic compounds are frequently used in the manufacture of pharmaceutical and agricultural chemicals. Fluorine is especially useful in such compositions because it can successfully mimic hydrogen in bioactive compounds due to the similar covalent radii of these two elements. Further its high electronegativity exerts pronounced electronic effects which alter the biological activities or chemical reactivities of fluorine-containing compounds. It is also recognized that fluorine incorporation leads to greatly increased lipid solubility, altering transport phenomena in biological systems. In fact, the trifluoromethyl group imparts more lipid solubility to a molecule than any other group known.

Perfluoroalkylated compounds are also used in such products as dyes, disinfectants, lubricants, and polymers. Important properties imparted by perfluoroalkyl groups in these uses include enhanced thermal and hydrolytic stability, lubricity, and hydrophobicity.

A primary use envisioned for perfluoroalkylated profen derivatives is as antiinflammatory and analgesic drugs. The profen moiety i.e. the arene-bound propionic acid group is a common feature of many peripherally-acting antiinflammatory and analgesic compounds. Examples include Ibuprofen, Flurbiprofen, Indoprofen, Pirprofen, Ketoprofen, Naproxen, and related compounds like Indobufen. The presence of a trifluoromethyl or other perfluoroalkyl group on such compounds may alter (should increase) the lipid solubility and, therefore, the bioavailability of the drugs.

The classical method of forming perfluoroalkyl aromatics involves the difficult photochemical side-chain chlorination of a alkyl aromatic compound to form a perchloroalkyl-substituted aromatic which in turn is reacted with hydrogen fluoride to effect a exchange of fluorine atoms for the chlorine atoms on the alkyl group. Ortho- and para-trifluoroalkylphenols and anilines are even more difficult to make. They have been synthesized by photochemical side-chain chlorination or bromination of the appropriate nitrotoluene to form the perhaloalky nitrobenzene. This product is treated with hydrogen fluoride to form the perfluoroalkyl nitrobenzene, which is then reduced to the perfluoroalkyl aniline. Diazotization and hydrolysis of the latter forms the perfluoroalkyl phenol.

In U.S. Pat. No. 4,634,787 the reaction between quinone and trichloromethyltrimethylsilane in tetrahydrofuran using tetrabutylammonium fluoride as catalyst to produce 4-(trichloromethyl)-4-(trimethylsilyloxy)-2,5-cyclohexadien-1-one is disclosed.

More recently perfluoroalkyl substituted compounds having gem-disubstituted cyclohexadienones in which the gem substituents are a perfluoroalkyl group and a hydroxy group have been claimed. These compounds are readily produced by reacting a quinone with a perfluoroalkyltrihydrocarbylsilane in the presence of an active catalyst and a proton source. These gem-di-substituted compounds in turn can be readily converted to perfluoroalkyl substituted aromatics. See for example application Ser. No. 177,097 filed Apr. 4, 1988.

The novel compounds of the present invention are those of the formula

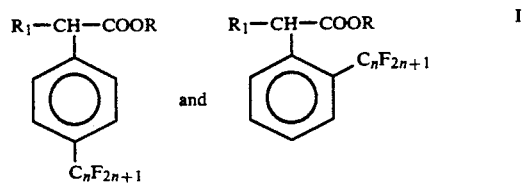

where n is an integer from 1 to 12 and R, $R_1$ are the same or different and are hydrogen or $C_1$ to $C_6$ linear or branched alkyl. Because the compounds of formula I bear an asymmetric center, racemic and both d&l enantiomeric forms are contemplated as part of this invention. The aromatic nucleus is typically substituted in the 1,4 position as shown. However, other substitution is possible at various locations on the aromatic ring e.g. 2-methyl, 2,5-diamino, etc. It is preferred that R and $R_1$ be the same or different and are the groups hydrogen, methyl, ethyl, n-propyl or 2-propyl. Particularly preferred are the compounds where R is hydrogen and $R_1$ is methyl. Especially, compounds with n equal to 1, 3, 6, 7 or 8 are preferred.

In cases where R is $C_1$ to $C_6$ linear or branched alkyl, the compounds of formula I are esters that can be readily hydrolyzed under normal saponification conditions, e.g. dilute alcohol solutions of sodium hydroxide.

Illustrative compounds of the present invention include
methyl 1-methyl-1-(4-perfluoroethylphenyl)acetate;
ethyl 1-methyl-1-[4-(perfluoro-1-hexyl)phenyl]acetate;
N-propyl 1-methyl-1-(4-perfluoromethylphenyl)acetate;
methyl 1-ethyl-1-(4-perfluoromethylphenyl)acetate;
ethyl 1-ethyl-1-(4-perfluoromethylphenyl)acetate;
N-propyl 1-ethyl-1-(4-perfluoromethylphenyl)acetate;
1-methyl 1-(4-perfluoromethylphenyl)acetic acid;
1-ethyl 1-(4-perfluoromethylphenyl)acetic acid;
methyl 1-methyl-1-(4-perfluoroethylphenyl)acetate;
ethyl 1-methyl-1-[4-(perfluoro-4-hexyl)phenyl]acetate;
N-propyl 1-methyl-1-(4-perfluoromethylphenyl)acetate;
methyl 1-ethyl-1-(4-perfluoromethylphenyl)acetate;
ethyl 1-ethyl-1-(4-perfluoromethylphenyl)acetate;
N-propyl 1-ethyl-1-(4-perfluoromethylphenyl)acetate;
1-methyl 1-(4-perfluoromethylphenyl)acetic acid;
1-ethyl 1-(4-perfluoromethylphenyl)acetic acid;
methyl 1-(4-perfluorooctylphenyl)acetate
ethyl 1-(4-perfluorooctylphenyl)acetate
methyl 1-(4-perfluoro-2-propylphenyl)acetate
ethyl 1-(4-perfluoro-2-propylphenyl)acetate
methyl 1-(2-perfluorooctylphenyl)acetate
ethyl 1-(2-perfluorooctylphenyl)acetate
methyl 1-(2-perfluoro-2-propylphenyl)acetate
ethyl 1-(2-perfluoro-2-propylphenyl)acetate
and the like.

As mentioned earlier, these compounds may be used as active intermediates for the preparation of biologically active compounds of the profen-type.

In order to prepare the novel compounds of formula I of this invention, and using the 4 (or para) position as illustrative a cyclohexatriene intermediate of the following formula is required

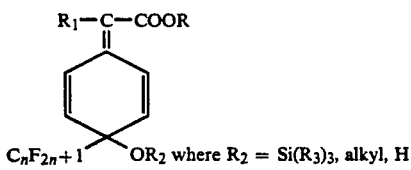    II where n, R and $R_1$ are as previously defined and $R_3$ is $C_1$ to $C_6$ linear or branched alkyl. The starting material for the 2-perfluoro substituted compounds uses the $C_nF_{2n+1}$ and $R_2$ moieties at the 2- (or ortho position.

The above gem-disubstituted cyclohexadienes of formula II are those having the perfluoroalkyl group and also a protected alcohol group. Because the compounds of formula II can be readily converted to the perfluroalkyl substituted aromatic compounds of formula I as well as other perfluorinated alkyl aromatics known in the prior art, the use of the photochlorination and then hydrogen fluoride halogen exchange process discussed earlier can be avoided.

Accordingly, the preferred synthetic route to prepare compounds of formula I from those of formula II involves the simple, relatively facile dissolving metal reduction process. Other reducing processes are also effective i.e. catalytic reducing systems such as those using platinum, palladium and the like or sodium borohydride, lithium aluminum hydride etc.

As such, the compounds of formula II can be selectively reduced by reaction with a metal in the presence of a proton donor. The metals typically of use herein include the alkali metals, lithium, sodium, and potassium—as well as calcium, zinc, magnesium, tin and iron. The alkali metals and calcium are effective as solutions in liquid ammonia, b.p. $-33°$ (the Birch reduction) in low-molecular weight aliphatic amines; in hexamethylphosphoramide; as very dilute solutions in ethers such as 1,2-dimethoxyethane; or as solutions in ether or tetrahydrofuran of certain alkali metal (potassium and cesium) complexes with macrocyclic polyethers (sometimes called crown ethers). Reactions with the metal solutions in liquid ammonia often use a cosolvent, such as ether, tetrahydrofuran, or 1,2-dimethoxyethane, to increase the solubility of the organic substrate in the reaction mixture. These same metals as well as zinc and magnesium have been used as suspensions in inert solvents such as ether, toluene, or xylene. For both procedures a proton source (frequently ethanol, isopropyl alcohol, t-butyl alcohol, or water) is present in the reaction medium, is added concurrently with the compounds of formula III or is added during the isolation. The preferred reactions are those where sodium amalgam, aluminum amalgam, zinc, zinc amalgam, tin or iron may be added directly to solutions of the compound II in hydroxylic solvents such as ethanol, isopropyl alcohol, n-butyl alcohol, isoamyl alcohol, acetic acid, water, or an aqueous mineral acid.

In order to prepare the compounds of formula II, it is necessary to use as a starting material the following compounds

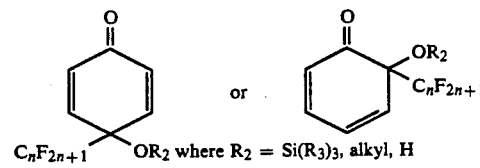    III where n and $R_3$ are as previously defined. These perfluoroalkyl dienones are treated with a phosphonate of the formula

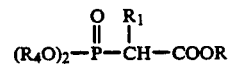

where R and $R_1$ are as previously defined and $R_4$ is $C_1$ to $C_6$ linear or branched alkyl or aryl to produce the compounds of formula II in good yields. The reaction of the compounds of formula III with the above phosphonate is a variation of the well known Wittig reaction where an aldehyde or ketone is treated with a phosphorus ylide (a phosphorane) to produce an olefin. See, for example, Johnson "Ylid Chemistry" Academic Press, Inc., New York, N.Y., 1966. The reaction is sometimes called the Horner-Emmons reaction. See Boutagy et al Chem. Rev. 74, 87-99 (1974). The phosphonate is more reactive then the corresponding phosphoranes used in the Wittig reaction. As such, reactions with ketones such as those compounds of formula III become possible.

The reaction with the phosphonates is very general. For example, while compounds of formula II are desired, the reaction can proceed more generally as follows:

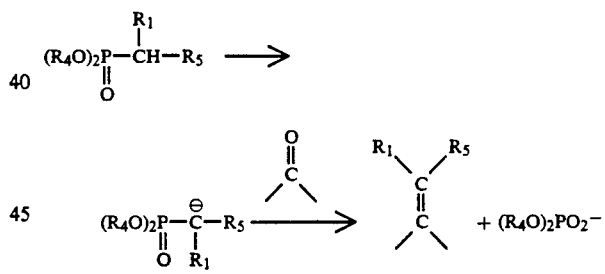

where $R_4$ is as previously described and $R_1$ and $R_5$ may be the same or different and include cyano, alkyl, alkyl ester and the like. Because the phosphorous product is a phosphate ester, separation from the olefinic product by water extraction is easily accomplished.

The compounds of formula III are prepared by reaction of a quinone or substituted quinone with a perfluoroalkyltrihydrocarbyl silane or by addition of perfluoroallyllithiums ($C_nF_{2n+1}$, where $n>2$) to quinones as set forth in copending applications Ser. Nos. 177,097; 177,151; 177,153 and 177,152; all of which were filed Apr. 4, 1988 and Ser. No. 337,186 filed Apr. 12, 1989 all of which are incorporated herein by reference.

Quinones that may be used in the process of this invention include mononuclear and polynuclear quinones, both 1,2-quinones and 1,4-quinones. Electron donating substituents, such as hydrocarbyl groups, hydrocarbyloxy groups, amino and mono- and dihydrocarbylamino groups, the hydroxyl group, and the like may be present in the quinones. A few exemplary quinones which may be used include 1,2-benzoquinone, 1,4-benzoquinone, 2-methyl-1,4-benzoquinone, 2-methoxy-1,4-benzoquinone, 2,5-dimethoxy-1,4-benzoquinone, 2-anilino-1,4-benzoquinone, 2,5-dianilino-1,4-benzoquinone, 2-phenyl-,1,4-benzoquinone, polyporic acid, the ubiquinones, 2,3-dimethyl-1,4-benzoquinone, 2,5-dimethyl-1,4-benzoquinone, 1,4-nephthoquinone, 1,2-naphthoquinone, Vitamin K$_1$, Vitamin K$_2$, 2-methyl-1,4-naphthoquinone anthraquinone, 2-methylanthraquinone, 2-ethylanthraquinone, 2-tert-butylanthraquinone, 1-aminoanthraquinone, 2-aminoanthraquinone, 1-amino-4-hydroxyanthraquinone, 1,2-diaminoanthraquinone, 1,4-diaminoanthraquinone, 1,5-diaminoanthraquinone, 2,6-diaminoanthraquinone, 1,8-diamino-4,5-dihydroxyanthraquinone, 1-hydroxy-4-(p-toluidino)anthraquinone, diphenoquinone, indanthrene blue, 1,2-dihydroxyanthraquinone, 9,10-phenanthraquinone, indanthrene violet, chrysophanic acid, and the like.

The perfluoroalkyltrihydrocarbyl silanes used in the process of this invention may be presented by the general formula:

R'SiR$_3$ where R' is a perfluoroalkyl group (trifluoromethyl, pentafluoroethyl, perfluorohexyl, etc.) and R, independently, is a hydrocarbyl group (alkyl, alkenyl, alkynyl, cycloalkyl, aryl, aralkyl, etc.). The number of carbon atoms in R and R' is irrelevant so long as the silane is co-reactive with the quinone in the process. A few illustrative compounds include trifluoromethyltrimethylsilane, tridecyltrifluoromethylsilane, trifluoromethyltrivinylsilane, triallyltrifluoromethylsilane, tricyclopentyltrifluoromethylsilane, tricyclopropylcarbinyltrifluoromethylsilane, trifluoromethyltriphenylsilane, trifluoromethyltri-(1-maphthyl)silane, tribenzyltrifluoromethylsilane, and corresponding and similar analogs containing the higher "homologous" perfluoroalkyl groups such as perfluoroethyl, perfluoropropyl, perfluoroisopropyl, perfluorobutyl, etc.

As noted above, this invention utilizes gem-disubstituted cyclohexadienones in which the gem substituents are a perfluoroalkyl group and a trihydrocarbylsiloxy group. In one preferred embodiment the perfluoroalkyl group is a trifluoromethyl group. In another preferred embodiment the trihydrocarbylsiloxy group is a trialkylsiloxy group. Particularly preferred compounds are those in which the gem substituents are a trialkylsiloxy group and a trifluoromethyl group.

Among the preferred subclasses of compounds useful to prepare the compounds of this invention are the following:

4-trialkylsiloxy-4-perfluoromethyl-2,5-cyclohexadien-1-ones;

4-trialkylsiloxy-4-perfluoromethyl-2,5-cyclohexadien-1-ones having an alkyl substituent in at least the 2 or 6 position;

1,4-dihydro-1-oxo-4-trialkylsiloxy-4-perfluoromethyl-naphthalenes;

2-trialkylsiloxy-2-perfluoromethyl-2,4-cyclohexadien-1-ones;

2-trialkylsiloxy-2-perfluoromethyl-2,4-cyclohexadien-1-ones having an alkyl substituent in at least the 4 or 6 position; and 9,10-dihydro-9-oxo-10-trialkylsiloxy-10-perfluoromethylphenanthrenes.

4-trialkylsiloxy-4-perfluoroethyl-2,5-cyclohexadien-1-ones;

4-trialkylsiloxy-4-perfluoroethyl-2,5-cyclohexadien-1-ones having an alkyl substituent in at least the 2 or 6 position;

1,4-dihydro-1-oxo-4-trialkylsiloxy-4-perfluoroethyl-naphthalenes;

2-trialkylsiloxy-2-perfluoroethyl-2,4-cyclohexadien-1-ones;

2-trialkylsiloxy-2-perfluoroethyl-2,4-cyclohexadien-1-ones having an alkyl substituent in at least the 4 or 6 position; and 9,10-dihydro-9-oxo-10-trialkylsiloxy-10-perfluoroethylphenanthrenes.

4-trialkylsiloxy-4-perfluoro-1-hexyl-2,5-cyclohexadien-1-ones;

4-trialkylsiloxy-4-perfluoro-1-hexyl-2,5-cyclohexadien-1-ones having an alkyl substituent in at least the 2 or 6 position;

1,4-dihydro-1-oxo-4-trialkylsiloxy-4-perfluoro-1-hexyl-naphthalenes;

2-trialkylsiloxy-2-perfluoro-1-hexyl-2,4-cyclohexadien-1-ones;

2-trialkylsiloxy-2-perfluoro-1-hexyl-2,4-cyclohexadien-1-ones having an alkyl substituent in at least the 4 or 6 position; and 9,10-dihydro-9-oxo-10-trialkylsiloxy-10-perfluoro-1-hexylphenanthrenes.

The practice and advantages of this invention will become still further apparent from the following illustrative examples. Examples I and II illustrate the preparation of perfluoroalkyltrihydrocarbylsilanes, the class of reactants used in the process of this invention.

EXAMPLE I

Triethyltrifluoromethylsilane

A flask equipped with a dry ice condenser was flame dried under a nitrogen stream, and charged with 25 g (0.17 mol) of chlorotriethylsilane and 40 mL of dichloromethane. After cooling the resulting solution to −78° C. and charging the condenser with dry ice and acetone, 40 mL (0.43 mol) of bromotrifluoromethane (Freon 13B1) that had been condensed into a graduated tube was warmed to room temperature and allowed to distill into the flask. The cold solution was treated dropwise with 66 mL (0.24 mol) of hexaethylphosphorous triamide, allowed to stir at −78° C. for two hours, and allowed to stir at room temperature overnight. Low boiling components were then short path distilled into a cold (−78° C.) receiving flask at >1 torr with the pot temperature kept at <50° C. The distillate was further fractionated by removal of the dichloromethane (40°–45° C. at atmospheric pressure) and short path distillation to give 22.0 g of 98% pure (69% yield) triethyltrifluoromethylsilane: bp 52°–54° C. at 10 torr; $^1$H NMR (CDCl$_3$)δ 0.59≧1.16 (m); $^{19}$F NMR (CDCl$_3$, relative to CFCl$_3$)δ-61.3 ppm (s); IR (neat) 2960, 2915, 2882, 1458, 1413, 1206, 1055, 1020, 734, 693 cm$^{-1}$; mass spectrum (70eV) m/z (relative intensity) 115 (66,M-CF$_3$), 105 (46), 87 (85), 77 (100), 59 (56), 49 (41), 47 (37), 41 (38). Anal Calcd. for C$_7$H$_{15}$F$_3$Si: C, 45.62; H, 8.20. Found: C, 45.59; H, 8.13.

EXAMPLE II

Tri-n-butyltrifluoromethylsilane

A flask equipped with a dry ice condenser was flame dried under a nitrogen steam, and charged with 5.0 g (20 mmol) of chlorotri-n-butylsilane and 10 mL of dichloromethane. After cooling the resulting solution to −78° C. and charging the condenser with dry ice and acetone. 6.2 mL (66 mmol) of bromotrifluoromethane (Freon 13B1) that had been condensed into a graduated tube was warmed to room temperature and allowed to distill into the flask. The cooling bath was removed and the mixture was allowed to warm to the temperature of the refluxing Freon (−59° C.). To this cold solution was added, dropwise, 8.0 mL (29 mmol) of hexaethylphosphorous triamide. The resulting solution was stirred at reflux for 1 hour. Removal of the condenser and continued stirring for 1 hour resulted in evaporation of excess Freon and warming of the solution to room temperature. Dilution with 30 mL of dichloromethane, water (three 30 mL portions) and 1N HCl (two 30 mL portions) washing, drying (MgSO$_4$), and concentration afforded a residue which was short path distilled to give 3.6 g (64% yield) of tri-n-butyltrifluoromethylsilane: bp 53°–58° C. at 0.5 torr; $^1$H NMR (CDCl$_3$) 0.60–1.10 (m, 5H), 1.10–1.56 (m, 4H); $^{19}$F NMR (CDCl$_3$, relative to CFCl$_3$)δ-61.6 ppm (s); IR (neat) 2956, 2925, 2872, 1214, 1058 cm$^{-1}$; mass spectrum (70eV) m/z (relative intensity) 199 (30,M-CF$_3$), 143 (80), 105 (30), 101 (27), 87 (30), 77 (66), 63 (43), 59 (41), 55 (54), 47 (25), 43 (20), 41 (100). Anal. Calcd. for C$_{13}$H$_{27}$F$_3$Si: C, 58.16; H, 10.14. Found: C, 58.26; H, 10.09.

Examples III and IV illustrate the gem-disubstituted compounds useful in this invention and methods by which they may be prepared.

EXAMPLE III

4-Triethylsiloxy-4-trifluoromethyl-2,5-cyclohexadien-1-one

A mixture of 83 mg (0.77 mmol) of 1,4-benzoquinone, 166 mg (0.9 mmol) of triethyltrifluoromethylsilane, and 1 mL of acetonitrile was treated with 22 mg (0.077 mmol) of tetrabutylammonium bifluoride and stirred at 25° C. for 30 minutes. Concentration of the mixture afforded a black oil which was purified by means of preparative thin layer chromatography (one 2 mm silica gel plate eluted with 50% dichloromethane-50% petroleum ether) to give 74 mg (33% yield) of 4-triethylsiloxy-4-trifluoromethyl-2,5-cyclohexadien-1-one.

EXAMPLE IV

4-Triethylsiloxy-4-trifluoromethyl-2,5-cyclohexadien-1-one

A mixture of 100 mg (1.3 mmol) of potassium bifluoride, 119 mg (1.1 mmol) of 1,4-benzoquinone, and 2 mL of acetonitrile was treated with 239 mg (1.3 mmol) of triethyltrifluoromethylsilane and stirred vigorously at room temperature for 2 hours. The mixture was filtered and the filter cake was washed with dichloromethane. Concentration of the combined filtrates gave a black oil which was dissolved in dichloromethane and loaded onto a column of silica gel. The column was washed with dichloromethane until the eluent contained no uV active material. Concentration of the eluent gave a colorless oil which was purified by PTLC (one 2 mm silica gel plate eluted with 50% dichloromethane-50% petroleum ether) to give 134 mg (41% yield) of 4-triethylsiloxy-4-trifluoromethyl-2,5-cyclohexadien-1-one.

Other starting compounds of this invention can be readily produced by procedures similar to those described in Examples III and IV.

EXAMPLE V

Methyl 2-(4-Triethylsiloxy-4-trifluoromethyl-2.5-cyclohexadienylidene acetate

Sixty percent sodium hydride (33 mg 0.82 mmol) was placed in a flame dried flask under a nitrogen atmosphere and washed free of mineral oil with three 1 mL portions of petroleum ether. Addition of 3 mL of dry diglyme followed by 133 L of trimethyl phosphonoacetate and stirring of the mixture for 10 minutes at room temperature resulted in formation of a white slurry. To this slurry was added 200 mg (0.68 mmol) of dienone of Example III or IV and the mixture was allowed to stir overnight. It was then poured into 25 mL of 1N HCl and the resulting aqueous mixture was extracted with three 10 mL portions of diethyl ether. Combination, drying (MgSO$_4$), and concentration of the organic layers afforded a residue which was purified by PTLC (one 2 mm plate eluted with 50% dichloromethane-50% petroleum ether) to give 150 mg (63% yield) of the ester as a pale yellow liquid. $^1$H NMR (CDCl$_3$) 0.55 (q, 6H, J=8 Hz), 0.91 (t, 9H, J=8 Hz), 3.76 (s, 3H), 5.81 (s, 1H), 6.15 (d, 1H, J=12 Hz), 6.20 (d, 1H, J=12 Hz), 6.45 (d, 1H, J=12 Hz), 7.90 (d, 1H, J=12 Hz); 13C NMR (CDCl$_3$) 5.9, 6.5, 51.5, 120.1, 123.9 (e, quartet, J=281 Hz), 126.3, 126.5, 131.0, 131.9, 139.7, 166.2; $^{19}$F NMR (CDCl$_3$)−80.3 (s); IR (thin film) 2953, 2909, 2876, 1708, 1456, 1406, 1380, 1365, 1309, 1267, 1235, 1175, 1112, 1077, 998, 868, 801, 745, 701, 611 cm$^{-1}$; high resolution mass spectrum calcd for C$_{16}$H$_{23}$F$_3$O$_3$Si 348.1369, found 348.1371.

EXAMPLE VI

Ethyl 2-(Diethylphosphono)propionate

A mixture of 5.1 mL (39 mmol) of ethyl 2-bromopropionate and 14 mL (79 mmol) of triethyl phosphite was heated to 130°–140° C. and 2.2 mL of bromoethane (bp 38°–45 ° C.) was collected by distillation. Then unreacted triethyl phosphite was removed by distillation (23°–85° C. at 6–0.2 torr), leaving 6.9 g (74% yield) of the above ester as a colorless liquid: $^1$H NMR (CDCl$_3$)δ 0.84–1.05 (m, 12H), 2.61 (d of q, 1H, J=23, 7 Hz), 3.60–3.85 (m, 6H).

EXAMPLE VII

Ethyl 2-(4-Triethylsiloxy-4-trifluoromethyl 2,5-cyclohexadienylidene)propionate

Sixty percent sodium hydride (33 mg, 0.82 mmol) was placed in a flame dried flask under a nitrogen atmosphere and washed free of mineral oil with three 1 mL portions of petroleum ether. Addition of 1mL of dry toluene followed by a solution of 200 mg of ethyl 2-(diethylphosphono)propionate and stirring of the mixture for 10 minutes at room temperature resulted in formation of a colorless solution. To this was added 200 mg (0.68 mmol) of the dienone of Example III or IV and the mixture was allowed to stir for one hour. It was then poured into 10 mL of 1N HCl and the resulting aqueous mixture was extracted with three 5 L portions of diethyl ether. Combination, drying (MgSO$_4$), and concentration of the organic layers afforded a residue which was purified by PTLC (one 2 mm plate eluted with 25% dichloromethane-75% petroleum ether) to give 160 mg (62% yield) of the ester as a colorless liquid: $^1$H NMR (CDCl$_3$) 0.55 (q, 6H, J=8 Hz), 0.92 (t, 9H, J=8 Hz), 1.34 (t, 3H, J=7 Hz), 2.13 (s, 3H), 4.28 (q, 2H, J=7 Hz), 5.95 (d, 1H, J=11 Hz), 6.09 (d, 1H, J=11 Hz), 6.85 (d, 1H, J=11 Hz), 7.32 (d, 1H, J=11 Hz); $^{13}$C NMR (CDCl$_3$)δ 6.1, 6.7, 14.2, 15.6, 61.1, 72.0 (e, quartet, J=26 Hz), 124.0 (e, quartet, J=281 Hz), 126.9, 127.2, 128.4, 129.3, 130.5, 131.1, 168.7; $^{19}$F NMR (CDCl$_3$)δ-81.8 (s); IR (thin film) 2953, 2909, 2876, 1708, 1456, 1406, 1380, 1365, 1309, 1267, 1235, 1175, 1112, 1077, 998, 868, 801, 745, 701, 611 cm$^{-1}$; high resolution mass spectrum calcd for C$_{18}$H$_{27}$F$_3$O$_3$Si 376.1682, found 376.1674.

EXAMPLE VIII

Methyl 2-(4-[Trifluoromethyl]phenyl)acetate

Aluminum foil (314 mg, 12 mg atom) was amalgamated by immersion in a solution of 2% mercuric chloride in water for 15 seconds, washed with absolute ethanol followed by diethyl ether, cut into small pieces, and added to a solution of 405 mg (1.2 mmol) of triene of Example II in 10 mL of 10% water-90% tetrahydrofuran. The resulting mixture was heated at 70° C. for one hour, allowed to cool to room temperature, and filtered. The filter cake was washed with tetrahydrofuran. Concentration of the combined filtrates gave a residue, which was poured into 20 mL of 1N HCl. The aqueous mixture was extracted with three 10 mL portions of diethyl ether. Combination, drying (MgSO$_4$), and concentration of the organic layers gave a residue, which was purified by PTLC (two 2 mm plates eluted with 50% dichloromethane-50% petroleum ether) to give 177 mg (70% yield) of the acetate as a colorless liquid: $^1$H NMR (CDCl$_3$) 3.69 (s, 2H), 3.71 (s, 3H), 7.40 (d, 2H, J=8 Hz), 7.59 (d, 2H, J=8 Hz); $^{19}$F NMR (CDCl$_3$)δ-63.1 (s); mass spectrum (70eV) m/z (relative intensity) 218 (36, M+), 199 (13), 159 (100), 140 (17), 109 (33), 105 (28), 59 (67); high resolution mass spectrum calcd for C$_{11}$H$_9$F$_3$O$_2$ 218.0555, found 218.0554.

EXAMPLE IX

Ethyl 2-(4-[Trifluoromethyl]phenyl)propionate

By a procedure identical to that used in Example VII, 28 mg (0.61 mmol) of triene of Example VI was reduced to give 97 mg (65% yield) of propionate as a colorless liquid: $^1$H NMR (CDCl$_3$) 1.21 (t, 3H, J=8 Hz), 1.51 (d, 3H, J=7 Hz), 3.78 (q, 1H, J=7 Hz), 4.12 (m, 2H), 7.42 (d, 2H, J=8 Hz), 7.59 (d, 2H, J=8 Hz); $^{19}$F NMR (CDCl$_3$)δ-63.0 (s); high resolution mass spectrum calcd for C$_{12}$H$_{13}$F$_3$O$_2$ 246.0876, found 246.0873.

EXAMPLE X 2-(4-[Trifluoromethyl]phenyl)propionic acid

A mixture of 1.93 g (7.8 mmol) of ethyl 2-(4-[trifluoromethyl]phenyl)propionate, 10 mL of 1N NaOH, and 10 mL of absolute ethanol was heated to reflux for 3 hours, allowed to cool to room temperature, and poured into 50 mL of 1N HCl. The resulting aqueous mixture was extracted with three 10 mL portions of dichloromethane. Combination, drying (MgSO$_4$), and concentration of the organic layers afforded an oil which was crystallized from hexanes to give 0.90 g (50% yield) of the acid as a white, crystalline solid: mp 56°-58° C.; $^1$H NMR (CDCl$_3$) 1.47 (d, 3H, J=7 Hz), 3.73 (q, 1H, J=7 Hz), 7.36 (d, 2H, J=8 Hz), 7.52 (d, 2H, J=8 Hz); $^{19}$F NMR (CDCl$_3$, relative to CFCl$_3$)−63.2 ppm (s); IR (neat) 2963, 1712, 1619, 1419, 1327, 1264, 1232, 1166, 1124, 1072, 1019, 843 cm$^{-1}$.

EXAMPLE XI

4-Hydroxy-4-perfluorohexyl-2,5-cyclohexadien-1-one

A mixture of 220 mg (2.0 mmol) of 1,4-benzoquinone, 0.48 mL (2.2 mmol) of perfluorohexyl iodide and 20 mL of dry diethyl ether was placed into a flame dried flask under a nitrogen atmosphere. The solution was cooled to −78° C. and treated dropwise with 1.46 mL (2.2 mmol) of a 1.5M solution of methyllithium-lithium bromide complex in diethyl ether. The solution turned blue on addition of the first drop of methyllithium and remained blue thereafter. After the addition, the mixture was stirred cold for 30 minutes and 6 mL of 1N HCl was added. The cold bath was removed and the blue color was discharged as the solution warmed to room temperature. The resulting solution was poured into 50 mL of 1N HCl and the aqueous layer was extracted with two 20-mL portions of diethyl ether. Combination, drying (MgSO$_4$), and concentration of the ether layers afforded a residue which was purified by PTLC (two 2 mm silica gel plates eluted with 1% methanol - 99% dichloromethane) to give 412 mg (54% yield) of 4-hydroxy-4-perfluorohexyl-2,5-cyclohexadien-1-one as a beige powder.

EXAMPLE XII

4-Hydroxy-4-perfluorooctyl-2,5-cyclohexadien-1-one

A mixture of 220 mg (2.0 mmol) of 1,4-benzoquinone, 1.2 g (2.2 mmol) of perfluorooctyl iodide and 20 mL of dry diethyl ether was placed into a flame dried flask under a nitrogen atmosphere. The solution was cooled to −78° C. and treated dropwise with 1.46 mL (2.2 mmol) of a 1.5M solution of methyllithium-lithium bromide complex in diethyl ether. The solution turned blue on addition of the first drop of methyllithium and remained blue thereafter. After the addition, the mixture was stirred cold for 30 minutes, and 6 mL of 1N HCl was added. The cold bath was removed and the blue color was discharged as the solution warmed to room temperature. The resulting solution was poured into 50 mL of 1N HCl and the aqueous layer was extracted with two 20-mL portions of diethyl ether. Combination, drying (MgSO$_4$), and concentration of the ether layers afforded a residue which was purified by PTLC (two 2 mm silica gel plates with 1% methanol-99% dichloromethane) to give 195 mg (15% yield) of 4-hydroxy-4-perfluorooctyl-2,5-cyclohexadien-1-one as a brown powder.

EXAMPLE XIII

4-Hydroxy-4-perfluoroisopropyl-2,5-cyclohexadien-1-one

A mixture of 220 mg (2.0 mmol) of 1,4-benzoquinone, 0.65 g (2.2 mmol) of 2-iodoperfluoroisopropane and 20 mL of dry diethyl ether was placed into a flame dried flask under a nitrogen atmosphere. The solution was cooled to −78° C. and treated dropwise with 1.46 mL (2.2 mmol) of 1.5M solution of methyllithium-lithium bromide complex in diethyl ether. The solution turned blue on addition of the first drop of methyl-lithium and remained blue thereafter. After the addition, the mixture was stirred cold for 30 minutes and 6 mL of 1N HCl was added. The cold bath was removed and the blue color was discharged as the solution warmed to room temperature. The resulting solution was poured into 50 mL of 1N HCl and the aqueous layer was extracted with two 20 mL portions of diethyl ether. Combination, drying (MgSO$_4$), and concentration of the ether layers afforded a residue which was purified by PTLC (two 2 mm silica gel plates eluted with 5% methanol - 95% dichloromethane) to give 114 mg (20% yield) of 4-hydroxy-4-perfluoroisopropyl-2,5-cyclohexadien-1-one as a brown solid which was recrystallized from dichloromethane.

EXAMPLE XIV

4-Methoxy-4-(perfluorohexyl)-2,5-cyclohexadien-1-one

Three mg (0.9 mmol) of tetrabutylammonium hydrogen sulfate and 4 mL of 50% NaOH was added to a solution of 200 mg (0.47 mmole) of 4-hydroxy-4-perfluorohexyl-2,5-cyclohexadien-1-one and 4 mL of toluene. The mixture was stirred for 10 minutes and 0.060 mL (0.63 mmol) of dimethyl sulfate was added. The mixture was stirred vigorously for an additional 2 hours, poured into 100 mL of 1N HCl, and 37% HCl was added until the solution was acidic to pH paper. The solution was extracted with three 50-mL portions of diethyl ether. Combination, drying (MgSO$_4$), and concentration of the diethyl ether layers afforded a residue which was purified by PTLC (two 2 mm silica gel plates eluted with dichloromethane) to give 162 mg (78% yield) of 4-methoxy-4-perfluorohexyl-2,5-cyclohexadien-1-one as a pale yellow oil.

EXAMPLE XV

4-Methoxy-4-perfluorooctyl-2,5-cyclohexadien-1-one

Three mg (0.9 mmol) of tetrabutylammonium hydrogen sulfate and 4 mL of 50% NaOH was added to a solution of 260 mg (0.49 mmol) of 4-hydroxy-4-perfluorooctyl-2,5-cyclohexadien-1-one and 4 mL of dichloromethane. The mixture was stirred for 10 minutes and 0.060 mL (0.63 mmol) of dimethyl sulfate was added. The mixture was stirred vigorously for an additional 2 hours, poured into 100 mL of 1N HCl, and 37% HCl was added until the solution was acidic to pH paper. The solution was extracted with three 50-mL portions of diethyl ether. Combination, drying (MgSO$_4$), and concentration of the diethyl ether layers afforded a residue which wa purified by PTLC (two 2 mm silica gel plates eluted with dichloromethane) to give 151 mg (57% yield) of 4-methoxy-4-perfluorooctyl-2,5-cyclohexadien-1-one as a pale yellow oil.

EXAMPLE XVI

Ethyl 2-(4-methoxy-4-perfluorohexyl-2,5-cyclohexadienylidene)propionate

To a flame dried flask under a nitrogen atmosphere was added 7 mg (0.2 mmol) of sodium hydride (60% dispersion in mineral oil). The mineral oil was removed by washing with three 1-mL portions of petroleum ether. The addition of 2 mL of dry toluene followed by 76 mg (0.32 mmol) of ethyl 2-(diethylphosphono)propionate followed by stirring for 10 minutes at room temperature resulted in a colorless solution. To this solution was added 76 mg (0.18 mmol) of 4-methoxy-4-perfluorohexyl-2,5-cyclohexadien-1-one. The mixture was stirred for 1 hour, poured into 10 mL of 1N HCl and extracted with three 5 mL portions of diethyl ether. Combination, drying (MgSO$_4$) and concentration of the diethyl ether layers afforded a residue which was purified by PTLC (one 2 mm silica gel plate eluted twice with 25% dichloromethane-75% petroleum ether) to give 77 mg (86% yield) of ethyl 2-(methoxy-4-perfluorohexyl-2,5-cyclohexadienylidene)propionate as a yellow oil.

EXAMPLE XVII

Ethyl 2-(4-methoxy-4-perfluorooctyl-2,5-cyclohexadienylidene)propionate

To a flame dried flask under a nitrogen atmosphere was added 4 mg (1.0 mmol) of sodium hydride (60% dispersion in mineral oil). The mineral oil was removed by washing with three 1-mL portions of petroleum ether. The addition of 1 mL of dry toluene followed by 59 mg (0.25 mmol) of ethyl 2-(diethylphosphono)propionate followed by stirring for 10 minutes at room temperature resulted in a colorless solution. To this was added 59 mg (0.1 mmol) of 4-methoxy-4-perfluorooctyl-2,5-cyclohexadien-1-one. The mixture was stirred for 1 hour, poured into 10 mL of 1N HCl, and extracted with three 5-mL portions of diethyl ether. Combination, drying (MgSO$_4$) and concentration of the diethyl ether layers afforded a residue which was purified by PTLC (one 2 mm silica gel plate eluted twice with 25% dichloromethane-75% petroleum ether) to give 35 mg (51% yield) of ethyl 2-(4-methoxy-4-perfluorooctyl-2,5-cyclohexadienylidene)propionate as a yellow oil.

EXAMPLE XVIII

Ethyl 2-(4-[Perfluorohexyl]phenyl)propionate

Aluminum foil (89 mg, 3.3 mg-atom) was amalgamated by immersion in a solution of 2% mercuric chloride in water for 15 s, washed with absolute ethanol followed by diethyl ether, cut into small pieces, and added to a solution of 116 mg (0.22 mmol) of ethyl 2-(4-methoxy-4-perfluorohexyl-2,5-cyclohexadienylidene)propionate in 2 mL of 10% water-90% tetrahydrofuran. The resulting mixture was heated at 70° C. for 1 hour, allowed to cool to room temperature, and filtered. The filter cake was washed with tetrahydrofuran. Concentration of the combined filtrates gave a residue, which was poured into 10 mL of 1N HCl and extracted with three 10-mL portions of diethyl ether. Combination, drying (MgSO$_4$), and concentration of the organic layers gave a residue which was purified by PTLC (one 2 mm silica gel plate eluted with 50% dichloromethane-50% petroleum ether) to give 100 mg (92% yield) of ethyl 2-(4-[perfluorohexyl]phenyl)propionate as a pale yellow oil.

EXAMPLE XIX

Ethyl 2-(4-Perfluorooctyl]phenyl)propionate

Aluminum foil (65 mg, 2.4 mg-atom) was amalgamated by immersion in a solution of 2% mercuric chloride in water for 15 s, washed with absolute ethanol followed by diethyl ether, cut into small pieces, and added to a solution of 84 mg (0.13 mmol) of ethyl 2-(4-methoxy-4-perfluorooctyl-2,5-cyclohexadienylidene) propionate in 2 mL of 10% H$_2$O-90% tetrahydrofuran. The resulting mixture was heated at 70° C. for 1 hour, allowed to cool to room temperature, and filtered. The filter cake was washed with tetrahydrofuran. Concentration of the combined filtrates gave a residue, which was poured into 10 mL of 1N HCl and extracted with three 10 mL portions of diethyl ether. Combination, drying (MgSO$_4$), and concentration of the organic layers gave a residue which was purified by PTLC (one 2 mm silica gel plate eluted with 50% dichloromethane-50% petroleum ether) to give 68 mg (85% yield) of ethyl 2-(4-[perfluorooctyl]phenyl)propinate as a pale yellow oil.

EXAMPLE XX 2-(4-[Perfluorohexyl]phenyl)propionic Acid

Ethyl 2-(4-[perfluorohexyl]phenyl)propionate (100 mg, 0.20 mmol) was dissolved in 5 mL of ethanol and 5 mL of 1N NaOH. The solution was heated to reflux for 1 hour, cooled to room temperature, poured into 30 mL of 1N HCl and extracted with three 10-mL portions of dicholormethane. Combination, drying (MgSO$_4$), and concentration of the organic layers gave a residue which was purified by PTLC (one 2 mm silica gel plate eluted with 15% methanol-85% dichloromethane) to give 54 mg (57% yield) of 2-(4-[perflurohexyl]phenyl)-propionic acid as a white powder.

EXAMPLE XXI 2-(4-Perfluorooctyl]phenyl)propionic acid

Ethyl 2-(4-[perfluorooctyl]phenyl)propionate (68 mg, 0.11 mmol) was dissolved in 5 mL of ethanol and 5 mL of 1N NaOH. The solution was heated to reflux for 1 hour, cooled to room temperature, poured into 30 mL of 1N HCl and extracted with three 10-mL portions of dichloromethane. Combination, drying (MgSO$_4$), and concentration of the organic layers gave a residue which wa purified by PTLC (one 2 mm silica gel plate eluted with 15% methanol-85% dichloromethane) to give 61 mg (94% yield) of 2-(4-[perfluorooctyl]phenyl)-propionic acid as a brown oil. The oil was recrystallized from dichloromethane to give brown crystals.

The compounds of the present invention display analgesic activity when used in this treatment of mammals.

I claim:

1. Compounds of the formula:

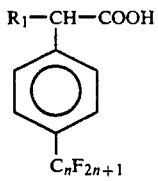

wherein n is an integer from 1 to 12, R$_1$ is C$_1$ to C$_6$ linear or branched alkyl and the physiologically active salts, alkyl esters and amides thereof and the enantiomers, mixtures, and racemates thereof.

2. The compounds according to claim 2 wherein n is 1.

3. The compounds according to claim 2 wherein n is 1.

4. The compounds in accordance with claim 1 wherein R$_1$ is methyl.

5. A process for producing compounds of the formula

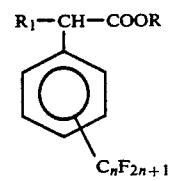

wherein the group C$_n$F$_{2n+1}$ is in position 2 or position 4 of the aromatic ring with respect to the group R$_1$-CH-COOR comprising treating a compound of the formula

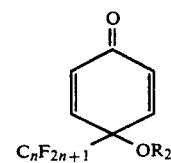

with

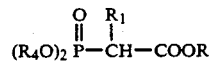

where n is an integer from 1 to 12, R and R$_1$ are the same or different and are hydrogen or C$_1$ to C$_6$ linear or branched alkyl and R$_2$=Si(R$_3$)$_3$, alkyl, H, and R$_3$ and R$_4$ are the same or different and are C$_1$ to C$_6$ linear or branched alkyl to form a compound of the formula

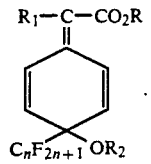

where n, R, R$_1$ and R$_2$ are as previously defined and reducing the compound of formula II.

6. The compounds according to claim 1 wherein n is 1, 3, 5, 7 or 8.

* * * * *